United States Patent [19]

Grasser et al.

[11] Patent Number: 4,819,257
[45] Date of Patent: Apr. 4, 1989

[54] LITHOTRIPSY WORK STATION

[75] Inventors: Franz Grasser, Eggolsheim; Sylvester Oppelt, Bamberg, both of Fed. Rep. of Germany

[73] Assignee: Siemens Aktiengesellschaft, Berlin and Munich, Fed. Rep. of Germany

[21] Appl. No.: 98,568

[22] Filed: Sep. 21, 1987

[30] Foreign Application Priority Data

Sep. 19, 1986 [DE] Fed. Rep. of Germany ....... 3631956

[51] Int. Cl.$^4$ ............................................. A61B 17/00
[52] U.S. Cl. ...................................... 378/99; 378/51; 378/62; 378/205; 128/328
[58] Field of Search ....................... 378/51, 62, 53, 99, 378/205; 358/111; 128/328

[56] References Cited

U.S. PATENT DOCUMENTS

| 4,262,306 | 4/1981 | Renner | 358/111 |
| 4,365,341 | 12/1982 | Lam | 378/205 |
| 4,609,940 | 9/1986 | Born et al. | |
| 4,705,026 | 11/1987 | Chaussy et al. | 378/177 |
| 4,730,351 | 3/1988 | Heumann | 378/99 |
| 4,741,008 | 4/1988 | Franke | 378/99 |

FOREIGN PATENT DOCUMENTS 0168559 1/1986 European Pat. Off. .
G8528785.1 7/1986 Fed. Rep. of Germany .
3617032 1/1987 Fed. Rep. of Germany ...... 128/328

Primary Examiner—Carolyn E. Fields
Assistant Examiner—David P. Porte
Attorney, Agent, or Firm—Hill, Van Santen, Steadman & Simpson

[57] ABSTRACT

A lithotripsy work station has a patient support table which is adjustable in three dimensions by a position control unit. The support table has an opening therein through which a shock wave generator can be coupled to a patient on the support table for disintegrating calculi in the body of the patient. An x-ray system is provided for identifying the position of the calculi within the patient, and a video chain is connected to the output of the x-ray system for providing a visual display of the calculi within the patient. A unit is connected to the table control unit which identifies the current position of the support table, and an arithmetic unit calculates the limits of the area or range within which the shock wave generator can be effectively coupled to the patient, given a particular table position. A video signal generator generates a video signal from the output of the arithmetic unit which is mixed with the patient image on the display, providing a visual representation of the range limits on the display screen.

4 Claims, 1 Drawing Sheet

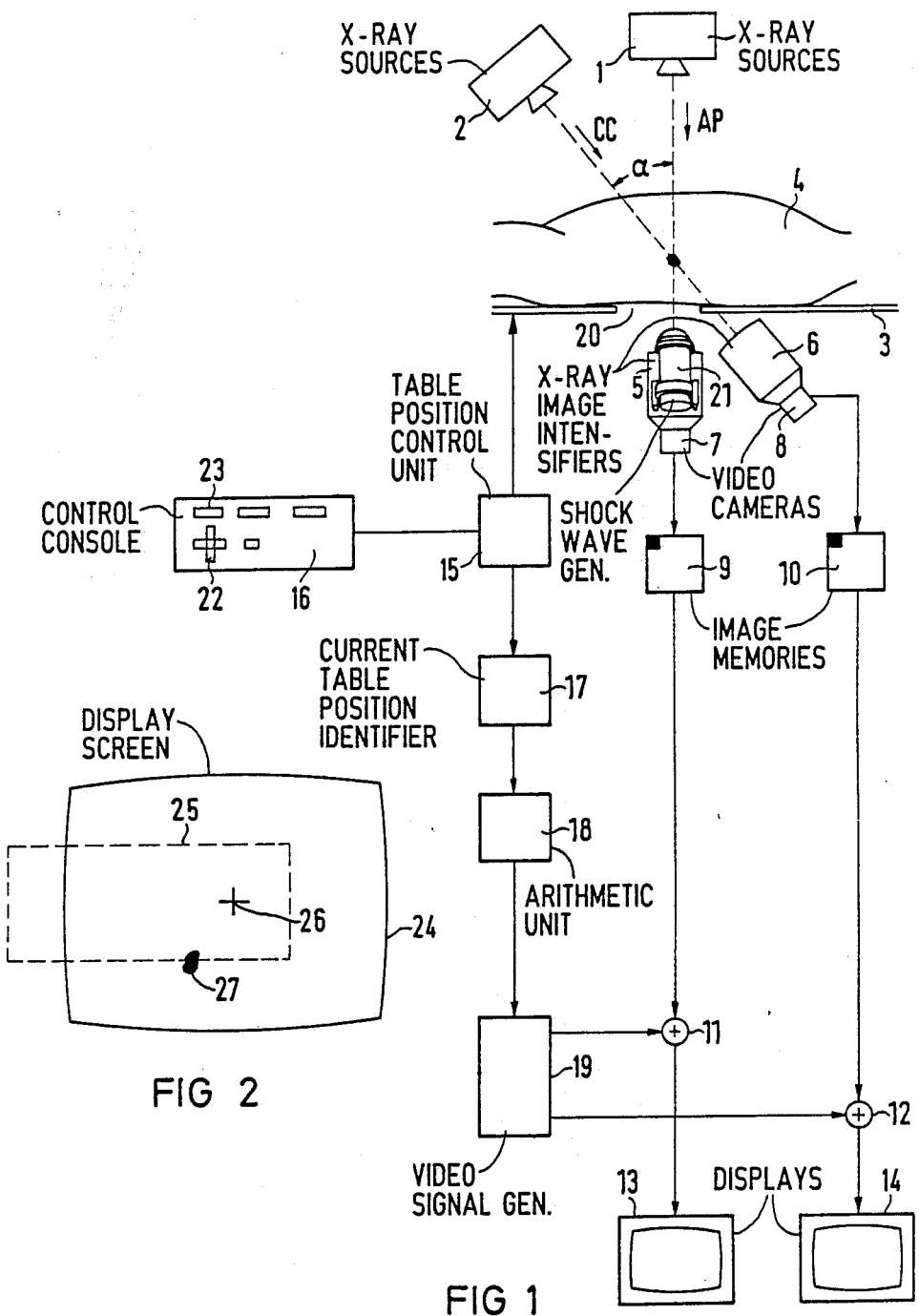

LITHOTRIPSY WORK STATION

BACKGROUND OF THE INVENTION

1. Field of the Invention

The present invention is directed to a lithotripsy work station, and in particular to a work station wherein an x-ray image of a patient with calculi is displayed on a screen to aid in positioning the calculi at the focus of a shock wave generator.

2. Description of the Prior Art

A lithotripsy workstation is disclosed in German Utility Model 85 28 785 wherein an x-ray system using two different x-ray sources for transradiating the patient from different angles, and having two shock wave generators which are pivotable from a standby position into an operating position. The x-ray sources generate intersecting x-ray beams and two image intensifier video chains are provided for representing the x-ray image. The two x-ray beams intersect at an isocenter, to which the shock wave generators are focussed in the operating position.

Pivoting or swiveling the shock wave generators is undertaken through a recess in the patient support table, so that a coupling of the shock wave generator can occur only at specific positions of the patient support table. When the calculus has been recognized by the x-ray examination system, and is moved to the isocenter by displacement of the patient support table, it is possible that effective coupling of the shock wave generator to the patient may not be present because the placement of the patient on the support table does not permit the calculus to be disposed at the isocenter because it is beyond the effective coupling region of the shock wave generators.

SUMMARY OF THE INVENTION

It is an object of the present invention to provide a lithotripsy work station wherein a determination can be made on the basis of the x-ray images of the patient as to whether effective coupling is possible by displacing the patient support table, or whether the patient must be moved relative to the support table.

The above object is achieved in accordance with the principles of the present invention in a lithotripsy work station wherein a table position control unit supplies an output to a unit which identifies the current position of the support table. An arithmetic unit calculates the region within which, given the position of the recess in the support table, effective coupling of the shock wave generator to the patient can occur. A video signal is generated based on the output of the arithmetic unit which displays the range limits for effective coupling on the display for the x-ray image by mixing a video signal with the conventional video signal from the x-ray system. The technician or physician can then immediately recognize by referring to the monitor picture whether a coupling of the shock wave generator to the patient is possible. If the calculus lies outside of the displayed range limits, the patient must be first moved on the patient support table before continuing the treatment.

The position of the isocenter with reference to the patient support table and the opening therein can be recognized from the monitor picture in an embodiment wherein the signal generator generates an image of a graticule identifying the center of the monitor picture, with the graticule being mixed into the video signal.

DESCRIPTION OF THE DRAWINGS

FIG. 1 is a block circuit diagram of a lithotripsy work station constructed in accordance with the principles of the present invention.

FIG. 2 shows a display screen for the station of FIG. 1 with a graticule mixed with the video signal.

DESCRIPTION OF THE PREFERRED EMBODIMENTS

A lithotripsy work station constructed in accordance with the principles of the present invention is shown in FIG. 1, the work station including an x-ray system having two x-ray sources 1 and 2 which generate respective x-ray beams penetrating a patient 4 disposed on a patient support table 3. The beams from the x-ray tubes 1 and 2, after being attenuated by the patient 4, are incident on respective luminescent input screens of x-ray image intensifiers 5 and 6. The x-ray tube 1 and the x-ray image intensifier 5 may be disposed such that a central ray of the x-ray beam from the x-ray source 1 is perpendicularly incident on the patient (a.p. projection). The x-ray source 2 and the x-ray image intensifier 6 may be obliquely arranged such that, for example, a central ray from the x-ray source 2 intersects the central ray from the x-ray source 1 at the isocenter inside the patient 4 at an angle $\alpha$ of, for example, 45° (c.c. projection). Transillumination images from the two different projection directions are thus obtained, so that the patient 4 can be shifted in three dimensions by moving the patient support table 3 so that, for example, a kidney stone or other type of calculus is disposed at the isocenter.

The patient support table 3 has an opening 20 therein. A shock wave generator (or generators) 21 are disposed below the patient support table 3 and are moveable, such as by pivoting, from a standby position into an operating position so as to be coupled to the patient 4 through the opening 20. The shock wave generator 21 has a membrane which is pressed against the skin of the patient 4 within the opening 20. This effectively couples the shock wave generator 21 to the patient 4 such that the focus of the shock wave generator 21 is coincident with the isocenter, so that shock wave treatment can be undertaken in the operating position and the calculus can be disintegrated.

Video cameras 7 and 8 are respectively coupled to the output screens of the x-ray image intensifiers 5 and 6. The respective output signals from the video cameras 7 and 8 are supplied to image memories 9 and 10. The output signals from the image memories 9 and 10 are connected to the inputs of respective addition stages 11 and 12. Each of the addition stages 11 and 12 has an output connected to a respective monitor 13 and 14 for visually reproducing the x-ray images.

After transillumination of the patient 4 has been undertaken using the x-ray sources 1 and 2, the x-ray images are converted into image signals by the image intensifiers 5 and 6 and the video cameras 7 and 8, which signals are stored in the memories 9 and 10. As described below, a signal is added to these conventional x-ray images in the addition stages 11 and 12, so that the x-ray images are displayed on the monitors 13 and 14 with a pattern mixed therein.

For three dimensional displacement of the patient support table 3, the table 3 is connected to a table position control unit 15 which effects motor-driven adjustment of the table position. The patient support table 3 is moved based on input signals supplied through a control console 16 connected to the table position control unit 15. The current position, in the three spatial coordinates, may be viewed on a display means 23 on the control console 16. A current table position identifier 17 is connected to the control unit 15 and generates an output signal corresponding to the current position of the patient support table 3. The output of the position identifier 17 is supplied to an arithmetic circuit 18 which uses this output to calculate the range limits of the coupling possibilities of the shock wave generator 21 on the basis of data contained in the arithmetic unit 18 identifying the relative position of the opening 20 in the patient support table 3. The calculated value from the arithmetic unit 18 is supplied to a signal generator 19, which generates a video signal on the basis of the signal from the arithmetic unit 18. The video signal generated by the video signal generator 19 is mixed with the video signals from the two video chains in the respective addition stages 11 and 12.

As shown in FIG. 2, the signal generated by the video signal generator 19 appears on the display screen 24 of each of the displays 13 and 14 as a mark or outline 25 which identifies the range limits of the area within which the shock wave generator 21 can be effectively coupled with the patient 4. The signal generator 19 may also mix a graticule 26 identifying the isocenter into the center of the display screen 24. The calculus 27 to be disintegrated, for example, a kidney stone, is also shown on the display screen 24. In this example, the calculus 27 is on the outline 25 of the range limits, and is not coincident with the isocenter identified by the graticule 26. Based on this display, the technician can perceive that a coupling of the shock way generator 21 to the patient 4 would be difficult to achieve. The patient 4 must be slightly re-positioned on the patient support table 3 before continuing treatment. A re-positioning of the patient 4 on the support table 3 would also be required if the calculus 27 were to lie outside of the outline 25. When, after the patient 4 has been re-positioned, the calculus 25 appears inside of the outline 25 identifying the range limits, coupling of the shock wave generator 21 with the patient 4 can ensue by displacing the patient support table 3 such that the calculus 27 is disposed in the isocenter identified by the graticule 26. This can be undertaken in three dimensions, for example, by operating elements 22 on the control console 16 until the graticule 26 and the calculus 27 are brought into coincidence in both display screens 24 of the monitors 13 and 14.

As a further possibility, the arithmetic unit 18 may also be connected to a circuit (not shown) for pivoting the shock wave generator 21 from the standby position into the operating position. Because the arithmetic unit 18 identifies the range limits of the coupling possibility of the shock wave generator 21, the circuit which effects pivoting can be supplied with an inhibiting signal preventing movement of the shock wave generator 21 into the operating position if the shock wave generator 21 is not located beneath the opening 20 in the patient support table 3. Damage to the shock wave generator 21 is thus avoided.

Although modifications and changes may be suggested by those skilled in the art it is the intention of the inventors to embody within the patent warranted hereon all changes and modifications as reasonably and properly come within the scope of their contribution to the art.

We claim as our invention:

1. A lithotripsy work station for use in disintegrating a calculus disposed in the body of a patient, said work station comprising:
   a support table on which said patient is disposed, said support table having an opening therein;
   means for three-dimensionally positioning said support table;
   x-ray means for generating at least one visually displayable image for identifying the position of said calculus in said patient;
   a shock wave generator having a focus, said shock wave generator adapted for coupling to said patient through said opening in said support table for disintegrating said calculus;
   means for identifying a current position of said support table;
   means for generating a signal based on the position of said opening within said patient support table corresponding to range limits for effective coupling of said shock wave generator to said patient;
   means for mixing said signal corresponding to the range limits with the viewable image of said patient; and
   means for simultaneously displaying the mixed signals.

2. A lithotripsy work station as claimed in claim 1, wherein said means for displaying has a display screen with a center, and further comprising means for generating a graticule identifying said center of said display screen, and means for mixing said graticule with said mixed signals.

3. A lithotripsy work station for use in disintegrating a calculus disposed in the body of a patient, said work station comprising:
   first x-ray means for generating a first x-ray image of said patient through a first plane of said patient;
   a first video chain for generating a first video image from said first x-ray image;
   a second x-ray means for generating a second x-ray image of said patient in a second plane of said patient;
   a second video chain for generating a second video image from said second x-ray image, said first and second planes intersecting in a line containing said calculus;
   a support table on which said patient is disposed, said support table having an opening therein;
   means for three-dimensionally positioning said support table;
   a shock wave generator having a focus, said shock wave generator positionable for coupling with said patient through said opening in said support table to disintegrate said calculus;
   means for generating a signal corresponding to a current position of said support table;
   means for generating a signal based on the relative positioning of said opening in said support table identifying a range within which said shock wave generator can be effectively coupled to said patient;
   means for generating a video signal corresponding to said range;
   means in each of said first and second video chains for mixing said video signal into each of said first and second video images;
   means in said first video chain for displaying said first video image mixed with said video signal; and means in said second video chain for displaying said second video image mixed with said video signal.

4. A lithotripsy work station as claimed in claim 3, wherein each of said means for displaying has a display screen with a center, and further comprising means for generating a graticule corresponding to said center of each of said display screens and for simultaneously mixing said graticule with said video signal for respective display with said first and second video images.

* * * * *